US00PP14343P29

(12) United States Plant Patent
Odom

(10) Patent No.: US PP14,343 P2
(45) Date of Patent: Dec. 2, 2003

(54) AZALEA PLANT NAMED 'CRIMSON QUEEN'

(50) Latin Name: *Rhododendron indicum*
Varietal Denomination: Crimson Queen

(76) Inventor: Richard Odom, 480 Butter Cemetery Rd., Forest Hill, LA (US) 71430

( * ) Notice: Subject to any disclaimer, the term of this patent is extended or adjusted under 35 U.S.C. 154(b) by 0 days.

(21) Appl. No.: 09/930,575

(22) Filed: Aug. 15, 2001

(51) Int. Cl.[7] ..... A01H 5/00
(52) U.S. Cl. ..... Plt./240
(58) Field of Search ..... Plt./240, 238

*Primary Examiner*—Kent Bell
(74) *Attorney, Agent, or Firm*—Jones, Walker, Waechter, Poitevent, Carrere & Denegre, LLP

(57) ABSTRACT

A new and distinct variety of semi-dwarf Azalea originated from a branch sport found on Azalea 'Crimson Princess'. The new variety possesses a unique red foliage, (178-A grayed-purple group) and is a semi-dwarf, with height about 24–30 inches.

14 Drawing Sheets

BACKGROUND OF THE INVENTION

The present invention relates to a new and distinct variety of evergreen azaleas botanically known as *Rhododendron indicum.* Richard Odom discovered this new azalea variety, hereinafter referred to as 'Crimson Queen', as a naturally occurring branch sport of an Azalea 'Crimson Princess', while 'Crimson Princess' originated as a naturally occurring whole plant sport of Azalea 'Crimson Majesty' which was originated as a naturally occurring branch sport of Azalea 'Red Formosa'. 'Red Formosa' is an unpatented azalea that is well-know in the trade in zones 7–9.

Tip cuttings were taken from branches of 'Crimson Princess' that seemed to grow larger and have larger leaves. The plants were then destroyed so as not to compromise the integrity of 'Crimson Princess'. Cuttings were then taken from subsequent plants as they matured. All work was undertaken at Country Pines Nursery, Inc. in Forest Hill, La. After several generations of asexual propagation from rooting cuttings, the present plant has been developed with unique coloration and semi-dwarf growth habitat.

Plant cuttings are allowed to root and grow in a 2.25 inch diameter (rosecup) container for 6–8 months, at which time the plant is about 3 inches in height, and is then transferred to a one gallon container. After an additional 10–12 months of growth, the plant is about 8–10 inches in height and about 8–10 inches in spread. At this time, the plant is sufficiently large for commercial sale as a one gallon plant. If larger plants are desired for commercial sale, the plant can be re-potted from the one gallon container to a three gallon container. An additional 8–10 months of growth in the three gallon container is generally needed to produce a commercial three gallon container plant, at about 18 inches in height and 20–22 inches in spread.

Patent applications have been filed herewith for Azalea 'Crimson Princess', U.S. patent application Ser. No. 09/930,574, a dwarf form developed from a naturally whole plant sport of 'Crimson Majesty', and azalea 'Crimson Majesty', U.S. patent application Ser. No. 09/930,573, a standard full form indicum developed from a branch sport of Azalea 'Red Formosa'. The three 'Crimson' azaleas have similar leaf coloration (187-A, 187-B, grayed purple group) and differ primary in growth size characteristics: 'Crimson Princess' being a dwarf (about 10–12 inches in height at about two ½ years from cutting), 'Crimson Queen' a semi-dwarf (about 16–18 inches in height at about 2½ years from cutting) and 'Crimson Majesty' being a standard ( about 24–28 inches in height at about 2½ years). See FIGS. 8 and 9. By contrast, the 'Red Formosa' is a standard azalea (about 24–28 inches at two ½ years from cutting, with an ultimate height of 5–8 feet). All of the 'Crimson' hybrid azaleas have strikingly different foliage coloration (187-A, 187-B, grayed purple group) from the 'Red Formosa' (N189A grayed green group). See FIGS. 2 and 9.

Asexual propagation of the new plant by rooting cuttings has been under Mr. Odom's direction at the same location. Several generations of the new plant have been evaluated and the distinctive characteristics of the plant have remained stable. The plant cannot be reproduced true from seed.

SUMMARY OF THE INVENTION

Crimson (greyed purple 187-A) on the upper and lower surfaces; shades of green somewhat more evident on the upper surface, less so on the lower. The crimson color is more intense on the new foliage and diminishes somewhat as the leaves age resulting in the older foliage having a deep crimson/green hue. Color differs significantly from standard 'Red Formosa' which has bright green foliage at all stages of maturity. Veins, especially the midvein and secondary veins, on the underside of the leaves on the 'Crimson Queen' semi dwarf retain the crimson color as the leaves grow older. The cultivar has a semi-compact growth habitat. The cultivar has a red-purple flower color similar to that of Azalea 'Red Formosa', but the blossom is not considered a novel feature.

The following are the most outstanding and distinguishing characteristics of this new cultivar when grown under normal horticultural practices in Forest Hill, La.

1. The unique foliage coloration, color greyed-purple group, 187-A.
2. Easily propagated with semi-hardwood cuttings in late spring through the summer.
3. Fast growth rate under normal fertilization and moisture conditions.
4. Upright, dense and globose in nature.
5. Small semi-compact growth habitat.

6. Makes a good container plant or under mid height or low height windows.
7. Useful in more confined landscape areas;
8. Groupings within landscape beds.

DESCRIPTION OF THE DRAWINGS

This new Azalea Hybrid variety is illustrated by the accompanying photographic prints in which:

FIG. 9 stems with foliage from all three 'Crimson' variety of plants adjacent to stems of 'Red Formosa'.

Figure 1:
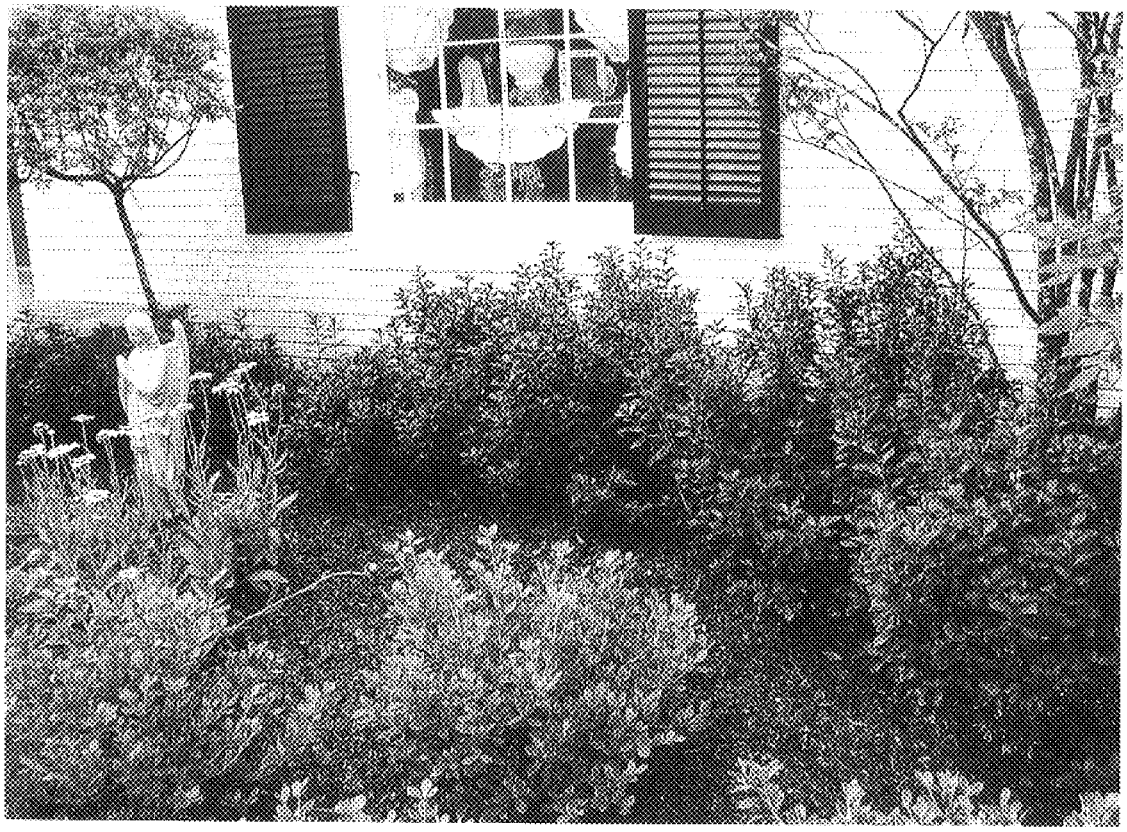
FIG. 1 is a view showing the 'Crimson' varieties of azaleas in place adjacent to the usual green colored leafed azaleas, demonstrating the difference in the plant's coloration to that of standard azaleas.
Figure 3:
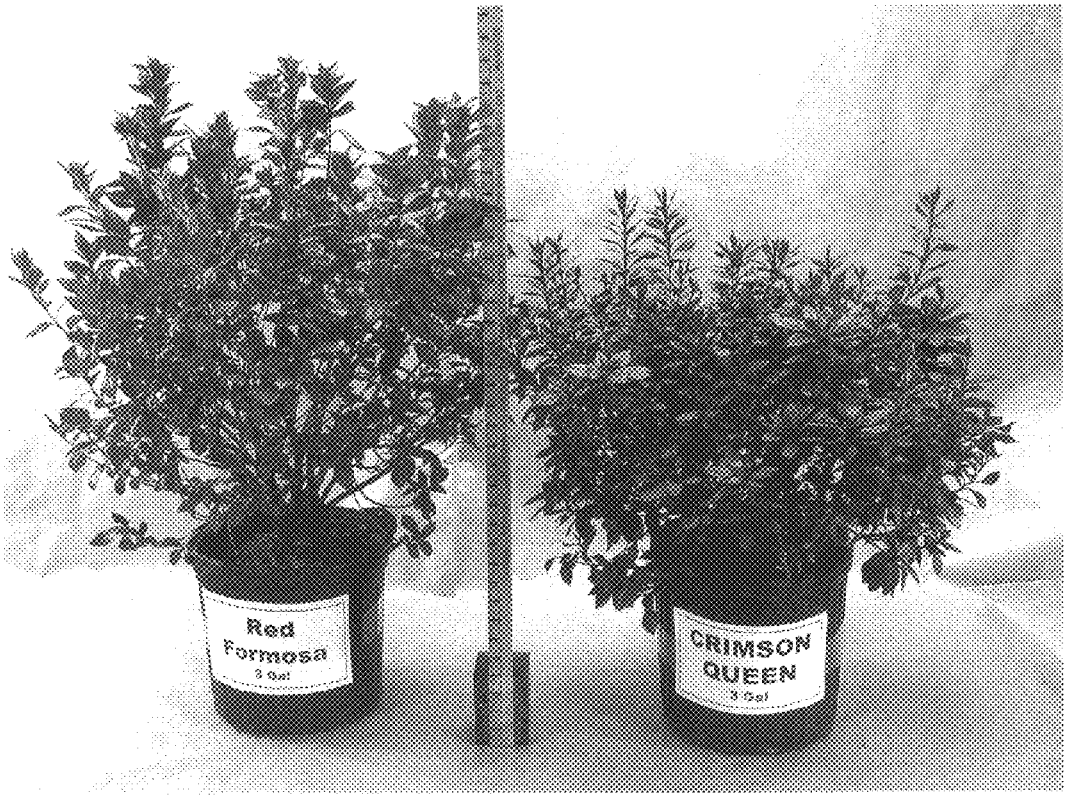
FIG. 3 shows the variety adjacent to the parent stock 'Red Formosa' of the 'Crimson' line.
Figure 2:
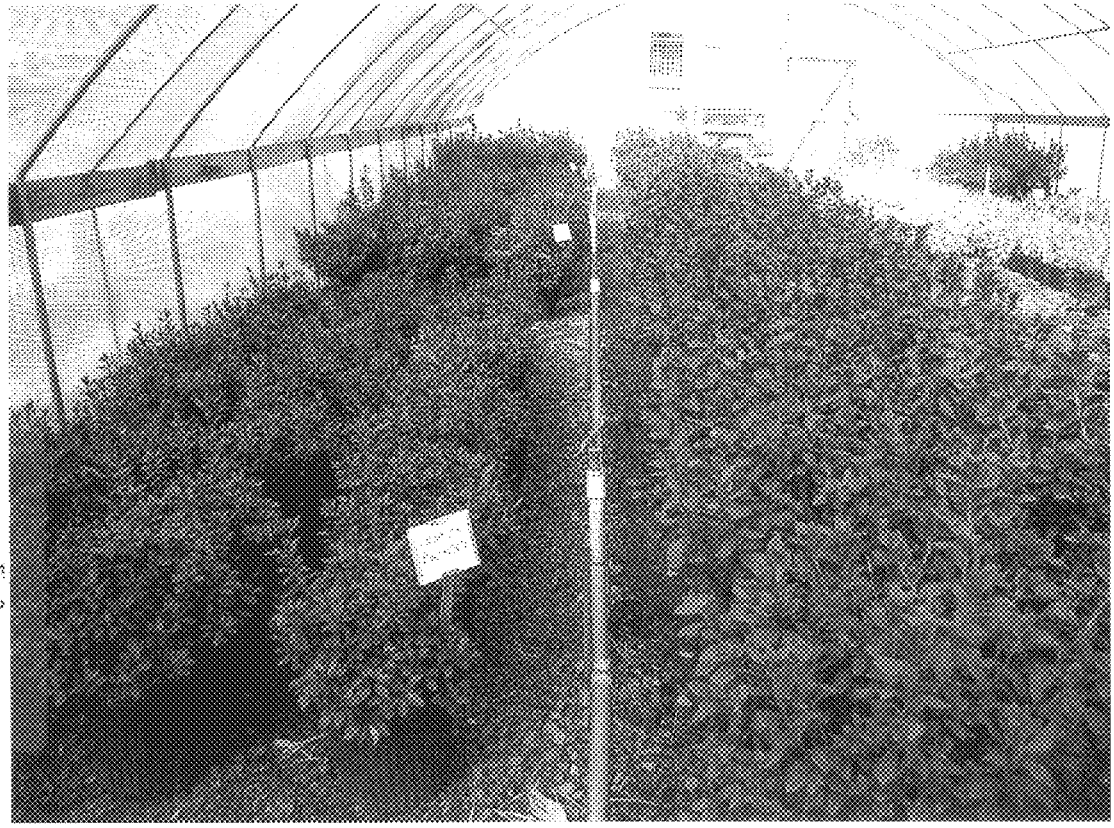
FIG. 2 is a view showing the 'Crimson' varieties in filtered light adjacent to 'Red Formosa' azaleas. 'Crimson Princes' is in the foreground, 'Crimson Queen' in the middle ground, and 'Crimson Majesty' in the background left of the photograph showing the difference in coloration from 'Red Formosa'. All plants are approximately 2.5 years of age from cuttings.

The colors shown are as true as is reasonably possible to obtain by conventional photographic procedures. The colors of the various plant parts are defined with reference to The Royal Horticultural Society Colour Chart. Description of colors in ordinary terms are presented where appropriate for clarity in meaning. Colors in the photographs may appear different than actual colors due to light reflectance. Color values cited in the Botanical Description of the Plant accurately describe the actual colors of the new Azalea.

DESCRIPTION OF THE PLANT 'CRIMSON QUEEN'

The following is detailed description of the new variety of Azalea based on my observations made of plants grown in wholesale commercial production practices, in greenhouses, and in established landscape plantings in Forest Hill, La., and was compiled with the assistance of Dr. Lowell E. Urbatsch, Director of the LSU Herbarium, Louisiana State University.

Botanical Description of the Plant

Scientific name: The plant belongs to a group of azaleas called the 'Southern Indian azaleas' or 'indicas' that are hybrids derived from various species of Rhododendron or derived directly from various species in that genus. *Rhododendron indicum* (L.) Sweet, although often given as the scientific name for this group of plants, has had little or no part in the parentage of the indicas. Most indicas are descendents of *Rhododendron simsii* Planch. *R. mucronatum* G. Don and/or *R. pulchrum* Sweet or their hybrids; in the industry, however, the accepted parentage is that of *Rhododendron indicum.*

Cultivar: 'Crimson Queen', a semi-dwarf indica azalea.

Growth habit: Shape of the plant at maturity: Broad compact, mound-forming shrubs. Individuals observed at about 2.5 years showed approximately 24–30 inches tall and 24–30 inches broad. It has not been observed as a mature plant in the landscape.

Branching habit: Sympodial (branching without a main axis but with many, more or less, equal laterals). One to several stems are evident at or near ground level that branch and re-branch frequently and at close intervals. Branches ascending or arcuate-ascending to upright. Branch characteristics (on mature growth of the current season): branch length, 10–18 cm; branch diameter, 3–5 mm; internode length, 4–10 mm.

Characteristics of the plant in winter dormancy: During the winter the plants are evergreen, i.e., the leaves remain on the stems. No signs of growth or flowering are evident during winter. Hardiness is expected to be the same as 'Red Formosa' cultivars. It has proven to be hardy in regard to winter cold and summer heat in the southern portion of zone 8.

Bark: Stem coloration on twigs is 178-B grayed-red group; bark coloration (on stems greater than 2 years old) is 177-B grayed-orange group. The stems, at least the lower ones, are rarely visible due to the compact leafy nature of the plants and, therefore, contribute little to its ornamental qualities.

Flowers:

Flower arrangement: Arranged singly or mostly in groups of 2–3 flowers at stem terminus; flowers face outward and upward.

Flower appearance: Corolla 5-lobed; star shaped; flaring open, 5.5–6 cm across (lobe tip to lobe tip); 4.5–5 cm deep; diameter at base of lobes is 2–2.5 cm; corolla lobes are spreading at right angles to long axis of the flower or slightly reflexed; corolla is a single whorl of petals, occasionally with 1–2 additional petals internal to the corolla, these smaller petals may be as long as 1.5 cm long and 0.5 cm wide and have a spatulate shape.

Flower bud: Rate of opening just after bud corolla becomes visible is about 2–3 days but rate is variable with temperature, sunlight, and possible other conditions.

Corolla color becomes visible when bud is about 12 mm long and 8 mm wide.

Flower bud shape is ovoid when viewed dosal-ventrally. When about 17 mm long and 10 mm wide the petals become visible and at about 4 cm long and 1.5–2 cm wide when the petals begin to open. In side view bud bulges slightly outward, inner surface is slightly concave. Overall, the bud has a somewhat falcate shape. As viewed from the top or in cross-section bud is slightly 5-lobed or 5 angeled. Color of corolla in bud stage is near 60-B (Fan 2, Royal Horticultural Society Colour Chart).

Petals: The petals are 5 in number and basally fused forming a corolla tube about 2.5 cm long; petal appearance is satiny; texture is smooth; petals are spatulate (obovate) and 4.5–5 cm long and 2–2.5 cm wide with rounded lobes; the lobes are somewhat undulate and margins of the lobes are entire to slightly crenate; margins are also undulate, sometimes strongly so giving the flower a ruffled appearance.

External and internal petal color of the corolla lobes is near 61-A (Fan 2, Royal Horticultural Society Colour Chart). The petals (corolla tube) are slightly lighter toward the base being close to color 61-B. Otherwise petal color is rather uniform.

Sepals: Sepals are fused basally forming a 5-lobed calyx; each sepal is approximately 15 mm long and 5 mm wide with the lowermost 4 mm of each fused together forming a calyx tube. The calyx lobes are approximately 1 cm long. Calyx diameter (sepal tip to sepal tip) is about 22 mm. Sepals are elliptic in shape and their margins are entire and the apex is acute. Sepals are moderately pubescent abaxially (outer surface) and glabrous adaxially (inner surface). Sepal color is close to 59-B (fan 2, purple group) on both inner and outer surfaces.

Peduncle: Peduncle (i.e., the stalk supporting a cluster of flowers) length is from 15–20 mm long and about 2 mm in diameter; it is somewhat flexible and it provides strong support for the flower; it is moderately pubescent with uniseriate hairs; and near 60-B (fan 2) in color.

Reproductive organs: Androecium consists of 9–10 stamens. Filaments are 2.5–3.5 mm long with a diameter of less than 1 mm; filament color is closest to 60-A; filaments are flexible and about the same length as the corolla or slightly exerted. Anthers are 1.5–2 mm long; oblong in shape; and closest to 79-B in color; pollen is a creamy white, 155-D, and produced in moderate amounts. Gynoecium appears to consist of 5 fused carpels. The ovary is densely pubescent (sericeous) with the hairs obscuring ovary surface; hairs are shiny and closest to 60-C in color; ovary shape is ovoid and about 5 mm long. The style is about 4.5–5 cm long, 1.5 mm in diameter and near 59-B in color. The stigma is truncate (i.e., having a flat surface) to slightly convex and circular to slightly lobed in end view with a diameter of 1.5 mm.

Leaves:

*Arrangement.*—Leaves alternate, that is one leaf per node. Leaves spaced about ¼ to 3/24 inches apart along the stems. Leaf stalk (petiole) about 3/16 to ½ inches long.

*Shape.*—Leaves elliptic to oblanceolate in outline; apices acute to acuminate; bases cuneate to rounded. Margins entire although somewhat ciliate.

*Size.*—½ to 1 inch broad and 1¼ to 2.5 inches long including the petiole.

Figure 10:
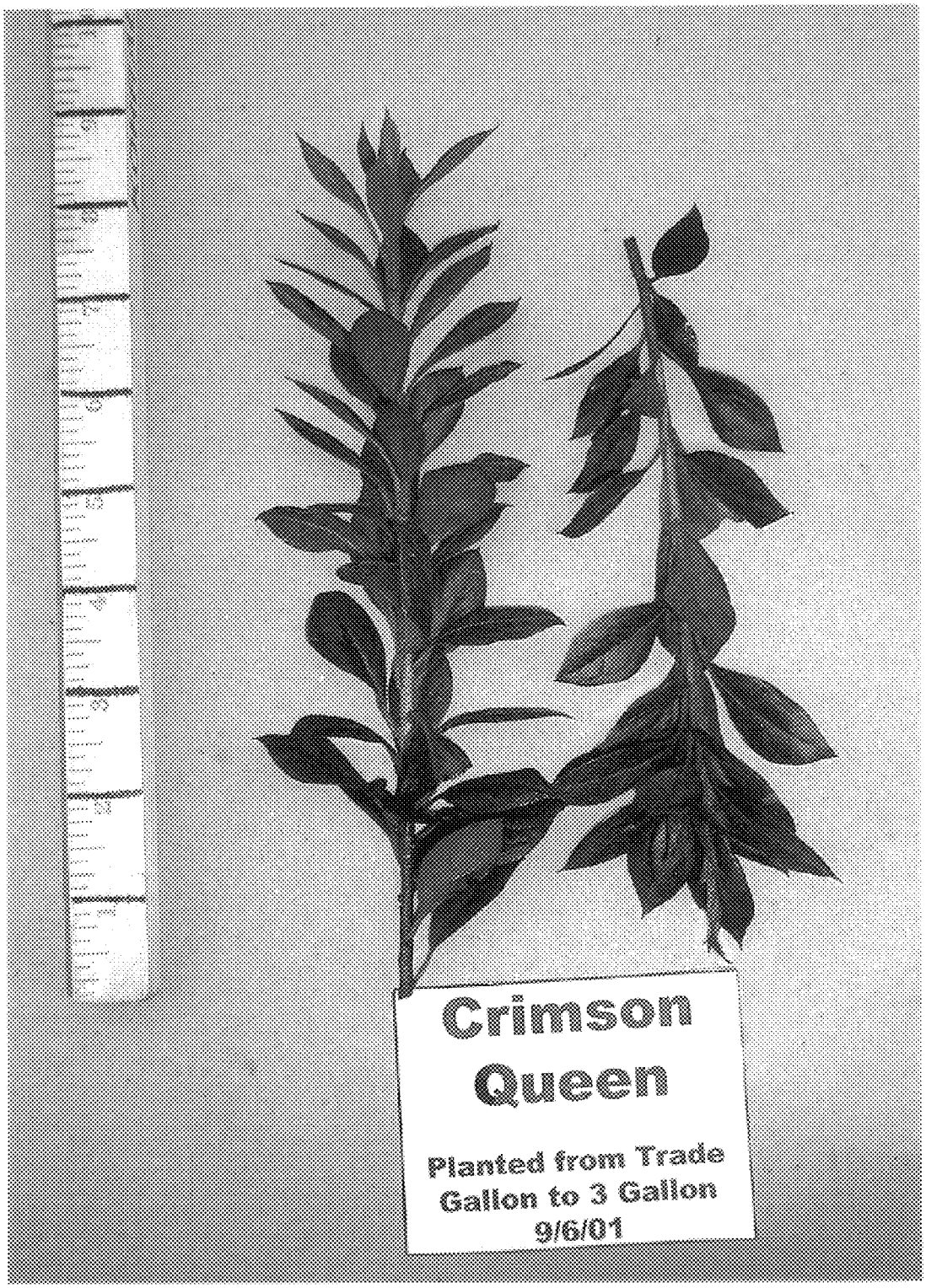
FIG. 10 show a close up of the stem and leaf structure of the instant variety showing the coloration.
Figure 11:
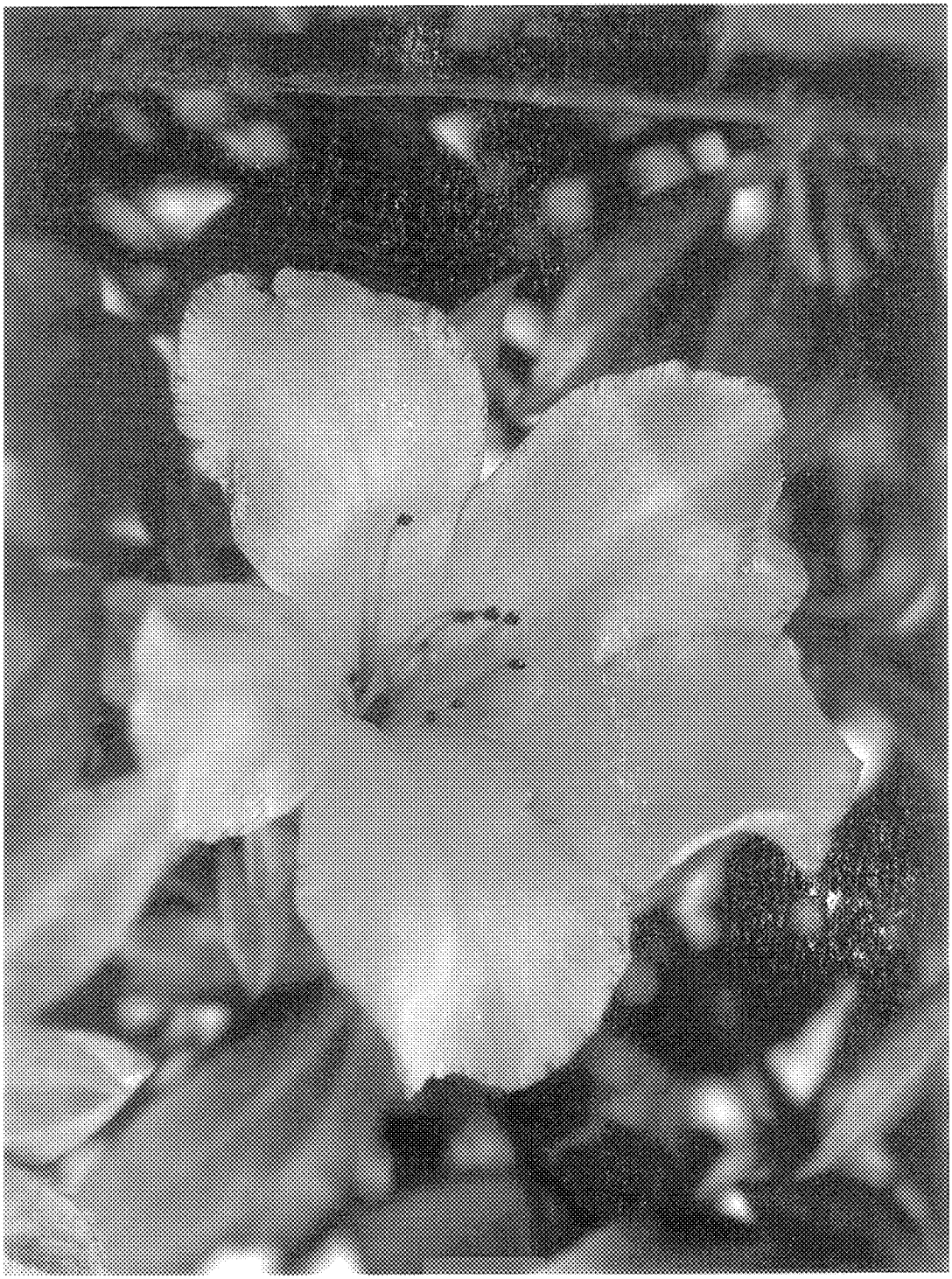
FIG. 11 shows a close up of a flower of the 'Crimson Queen' variety.
Figure 12:
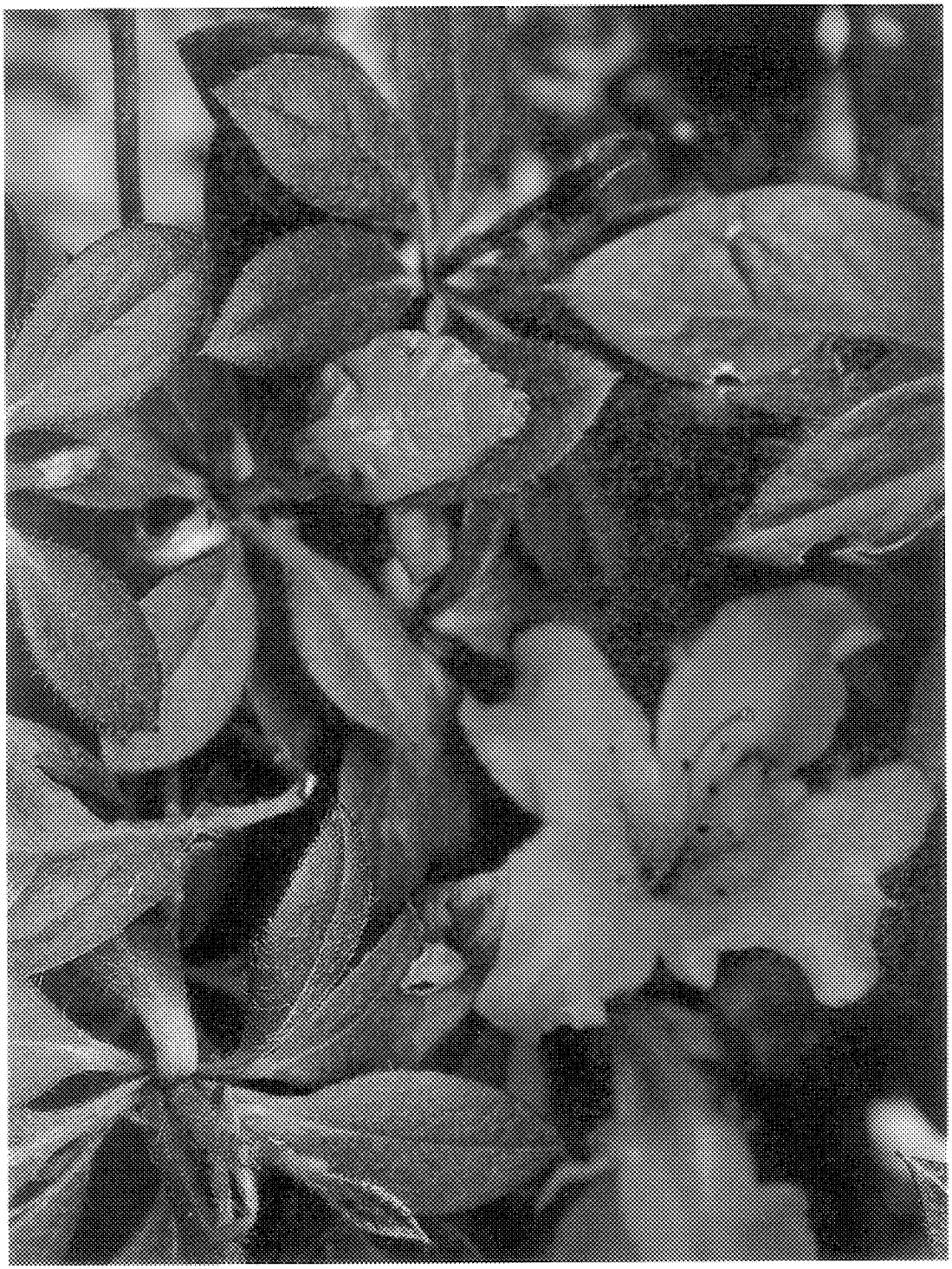
FIG. 12 shows a close up of a bud representative of the 'Crimson Queen' variety.
Figure 13:
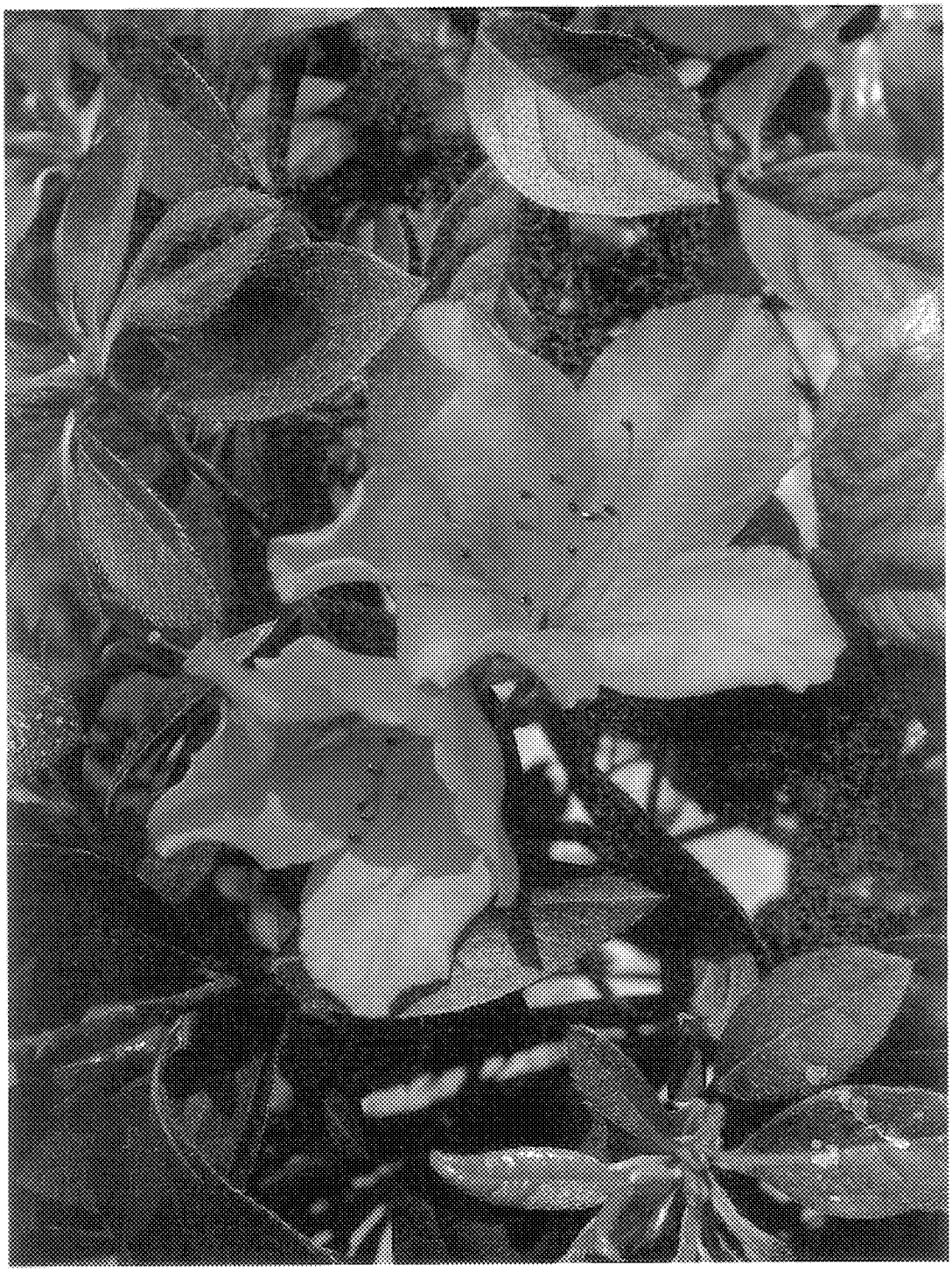
FIG. 13 shows a close up of a flower from the 'Red Formosa' variety.
Figure 14:
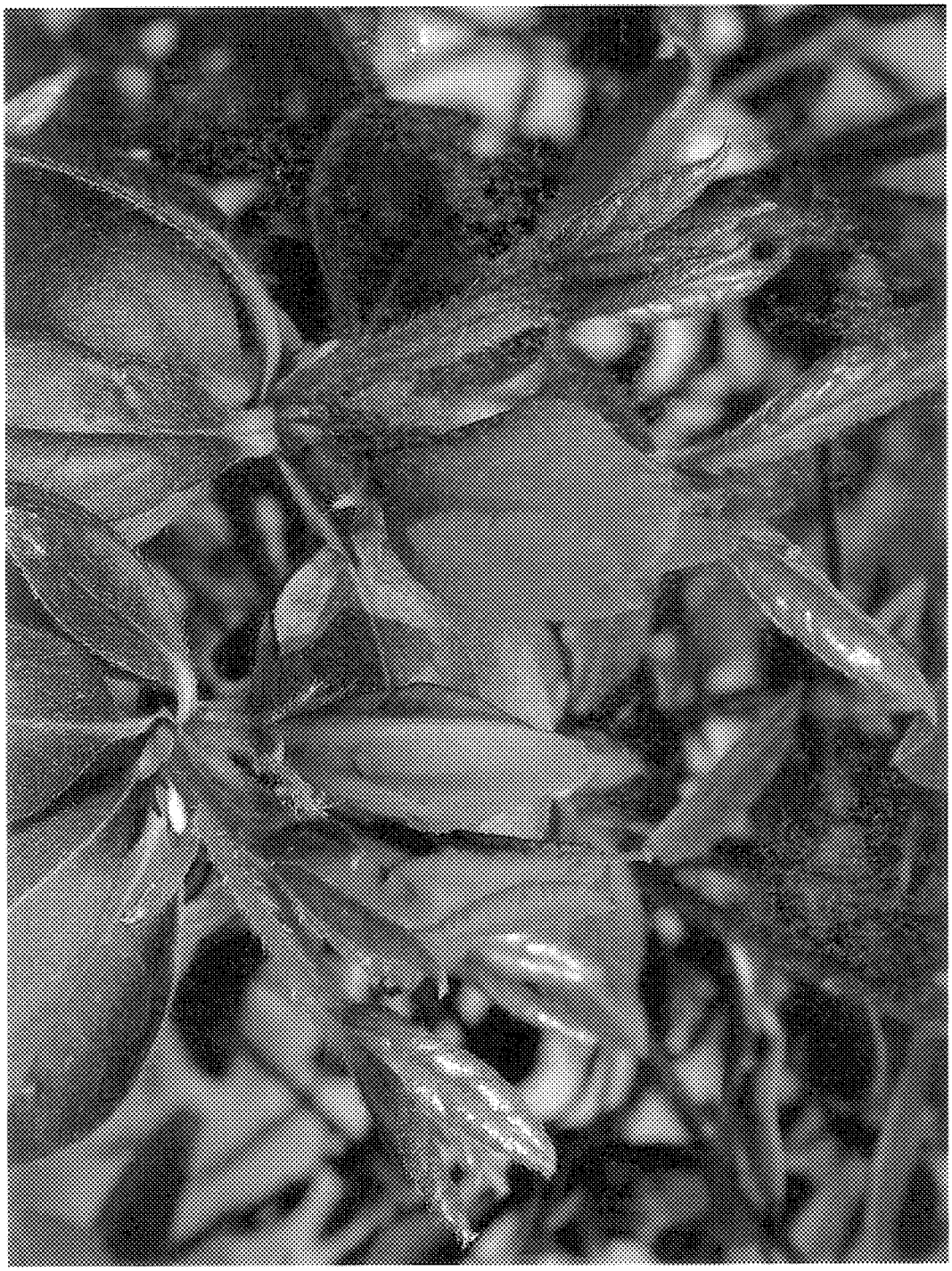
FIG. 14 shows a close up of a bud from the 'Red Formosa' variety.

*Color.*—Crimson on the upper and lower surfaces; shades of green somewhat more evident on the upper surface, less so on the lower. The crimson color is more intense on the new foliage and diminishes somewhat as the leaves age resulting in the older foliage having a deep crimson/green hue. Color differs significantly from standard 'Red Formosa' which has bright green foliage at all stages of maturity. See FIG. 9. Veins, especially the midvein and secondary veins, on the underside of the leaves on the 'Crimson Queen' retain the crimson color as the leaves grow older. See FIG. 10. The foliage of 'Crimson Queen' is lighter than that of 'Crimson Princess' but darker that of 'Crimson Majesty' in appearance. See FIG. 9.

The Royal Horticultural Society Colour Chart was used as per their instructions in order to better quantify the colors of the leaves. The results are summarized in the following Table 1.

TABLE 1

| Age of leaves | Feature | RHS color group | Best color match | Variation among leaves |
|---|---|---|---|---|
| Newly formed leaves | Upper surface | Greyed-Purple Group | 187-A | — |
| | Lower surface | Greyed-Purple Group | 183-B | — |
| | Veins, lower surface | Greyed-Purple Group | 185-A | — |
| Mature leaves | Upper surface[1] | Greyed-Purple Group | 187-A | 139-A, Green Group |
| | Lower surface[1] | Greyed-Purple Group | 184-B | 137-B, Green Group |
| | Veins, lower surface | Greyed-Purple Group | 187-B | — |

[1]The mature leaves appear to be a blending of the green and reddish colors resulting in the greyed purple color. However, the green is somewhat more evident in the mature leaves compared to the younger ones.

Figure 4:
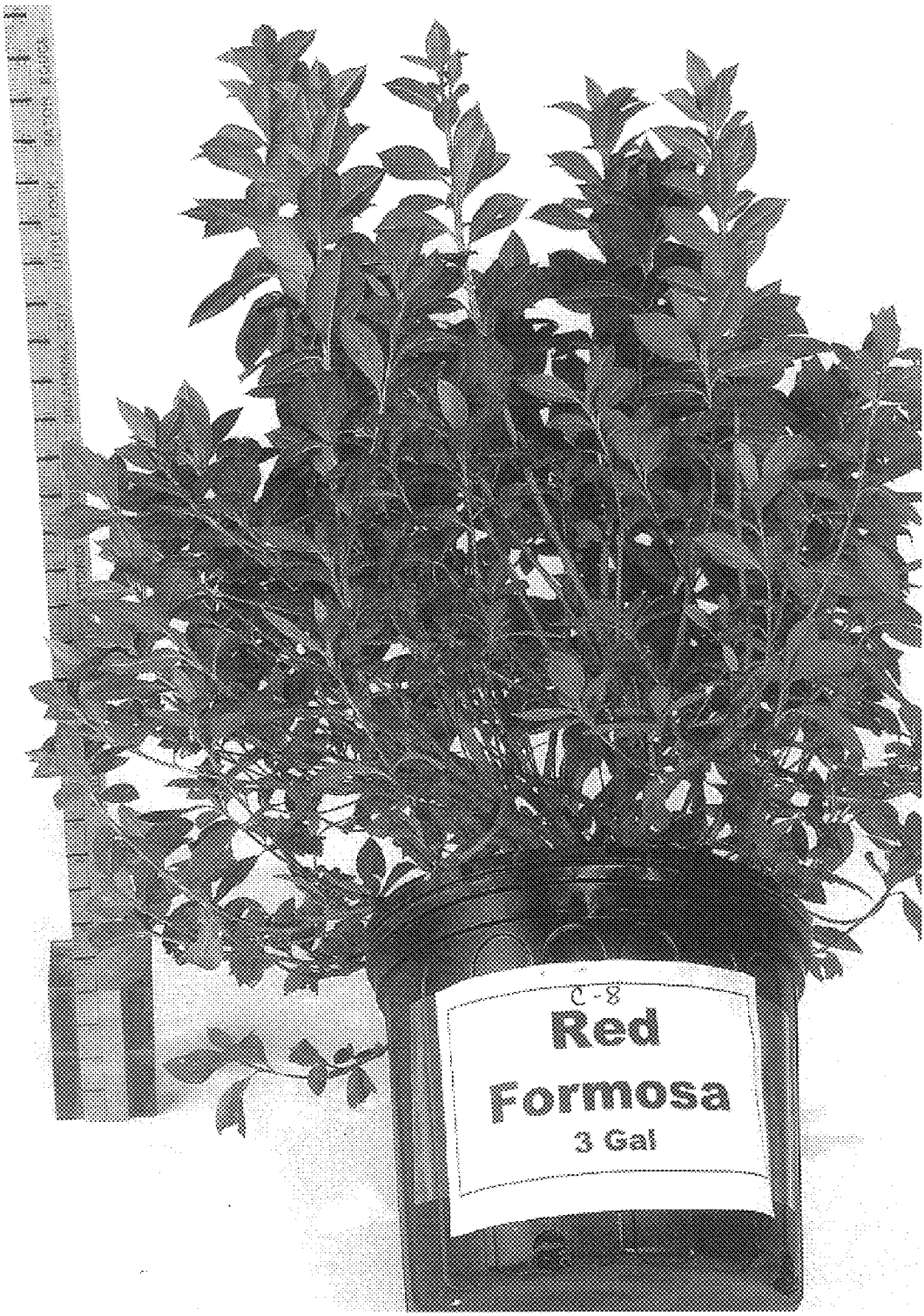
FIG. 4 shows the foliage and stem color of the underside of the foliage of 'Red Formosa' the parent stock of the 'Crimson' varieties.
Figure 5:
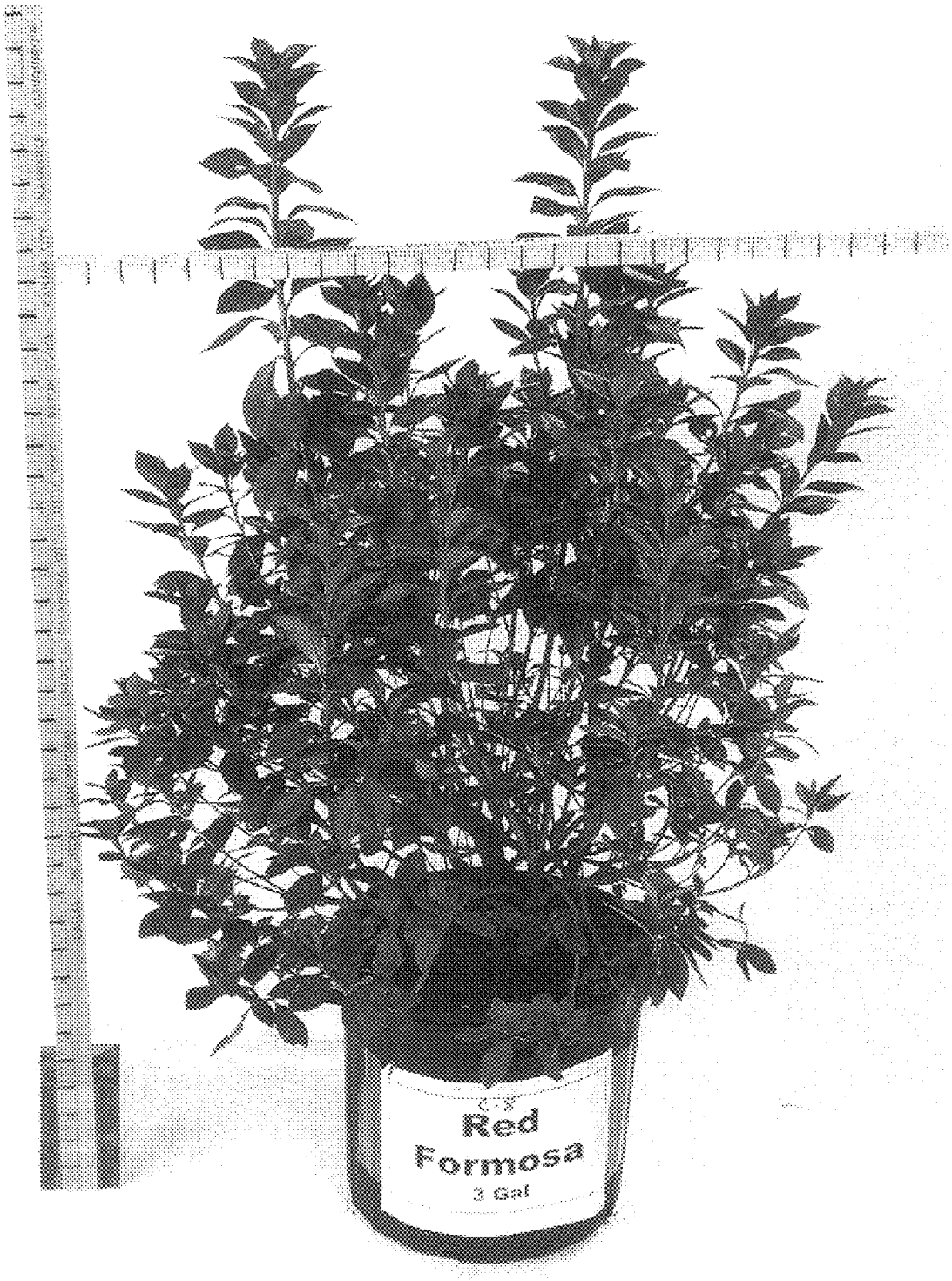
FIG. 5 shows the foliage and stem color of the upper surface foliage of 'Red Formosa' the parent stock of the 'Crimson' varieties.
Figure 6:
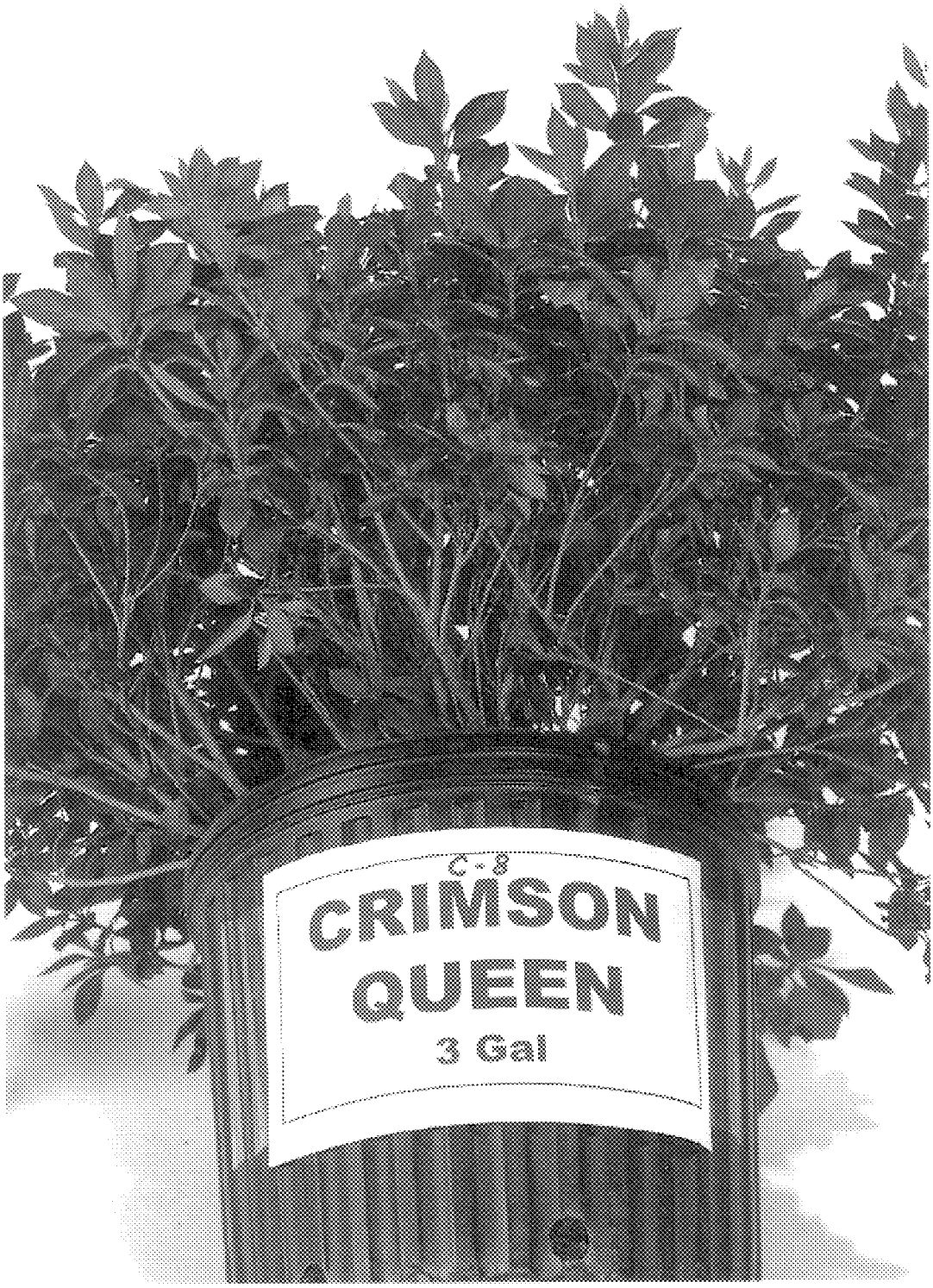
FIG. 6 shows the dense, upright and globose growth habit of a three gallon plant 2.5 year old plant of the instant variety showing foliage and stem color of the underside surface of the foliage.
Figure 7:
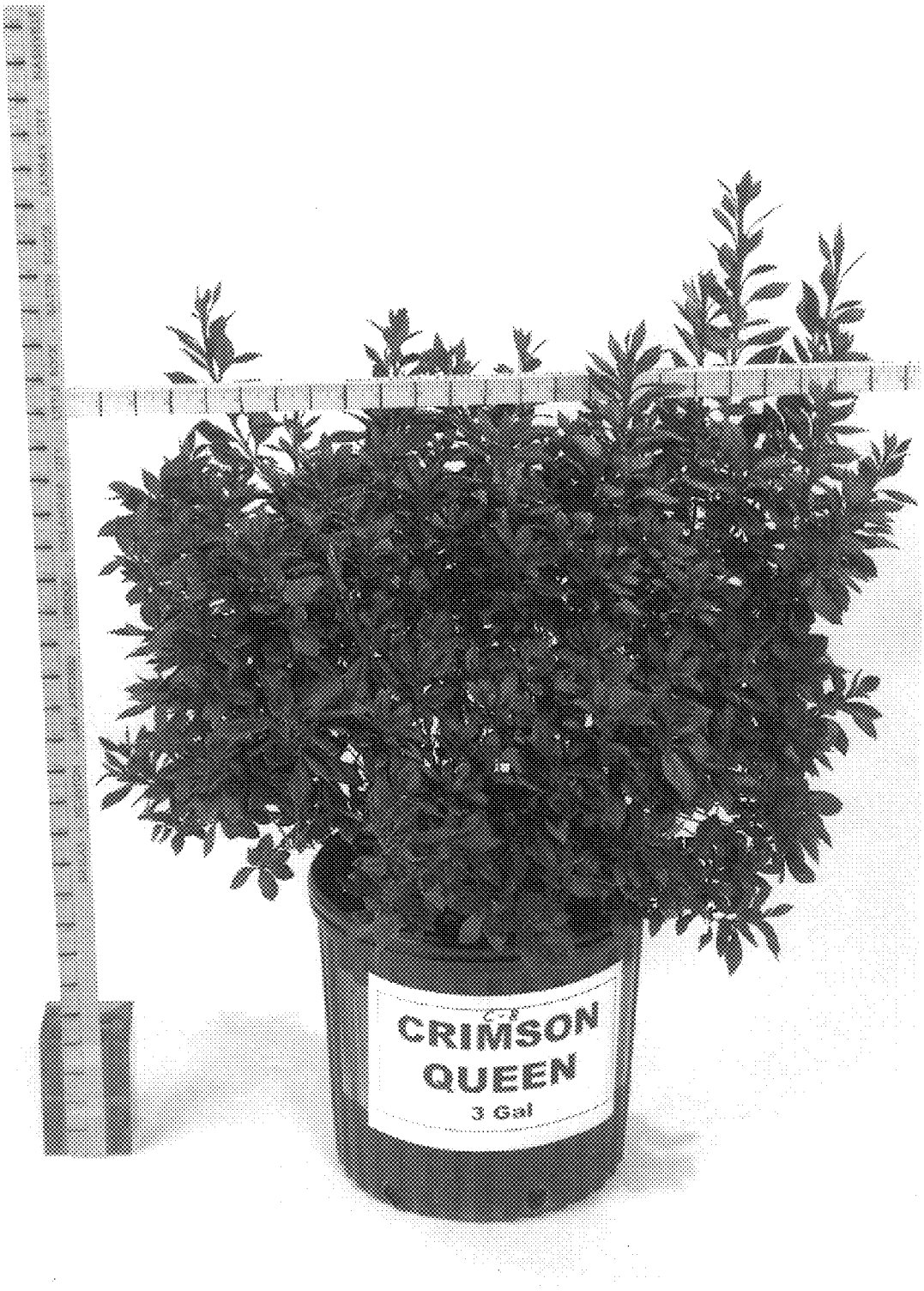
FIG. 7 shows the dense, upright and globose growth habit of a three gallon plant 2.5 year old plant of the instant variety showing foliage and stem color of the upper surface of the foliage.
Figure 8:
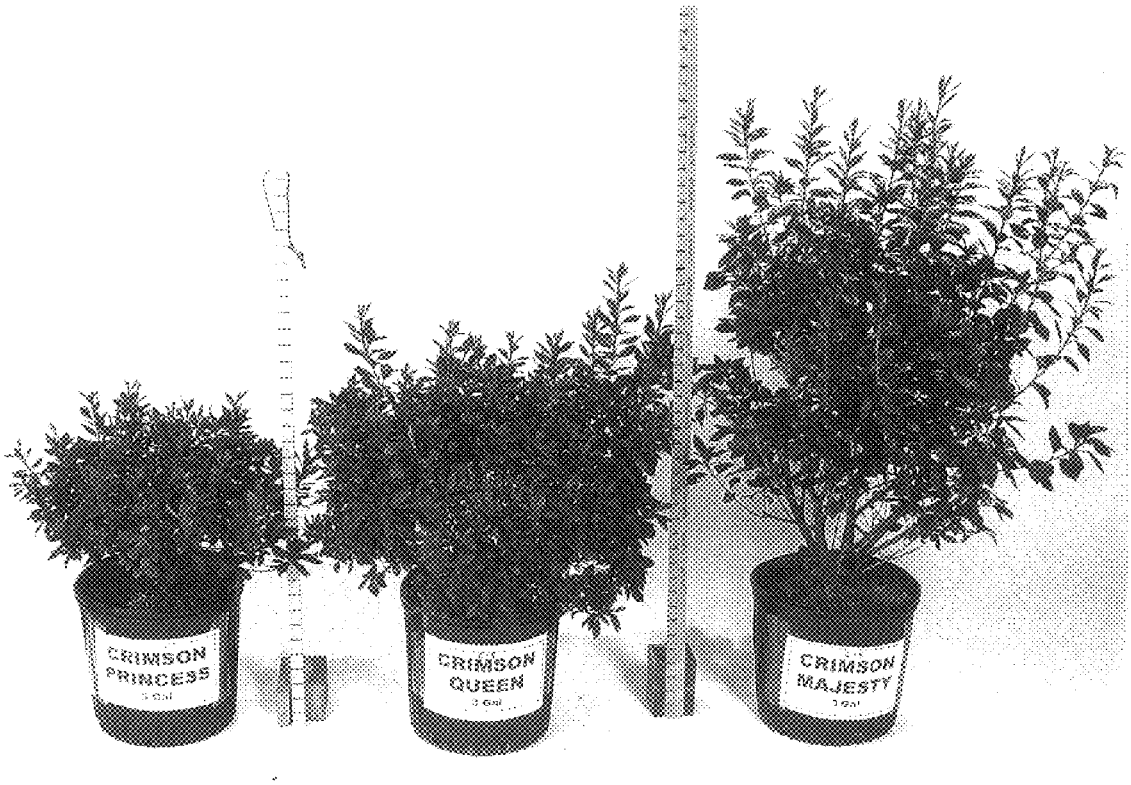
FIG. 8 shows the three 'Crimson' variety plants adjacent each other to show the distinction in plant growth characteristics, all plants being about 2.5 years of age from cuttings in a three gallon container.
Figure 6:
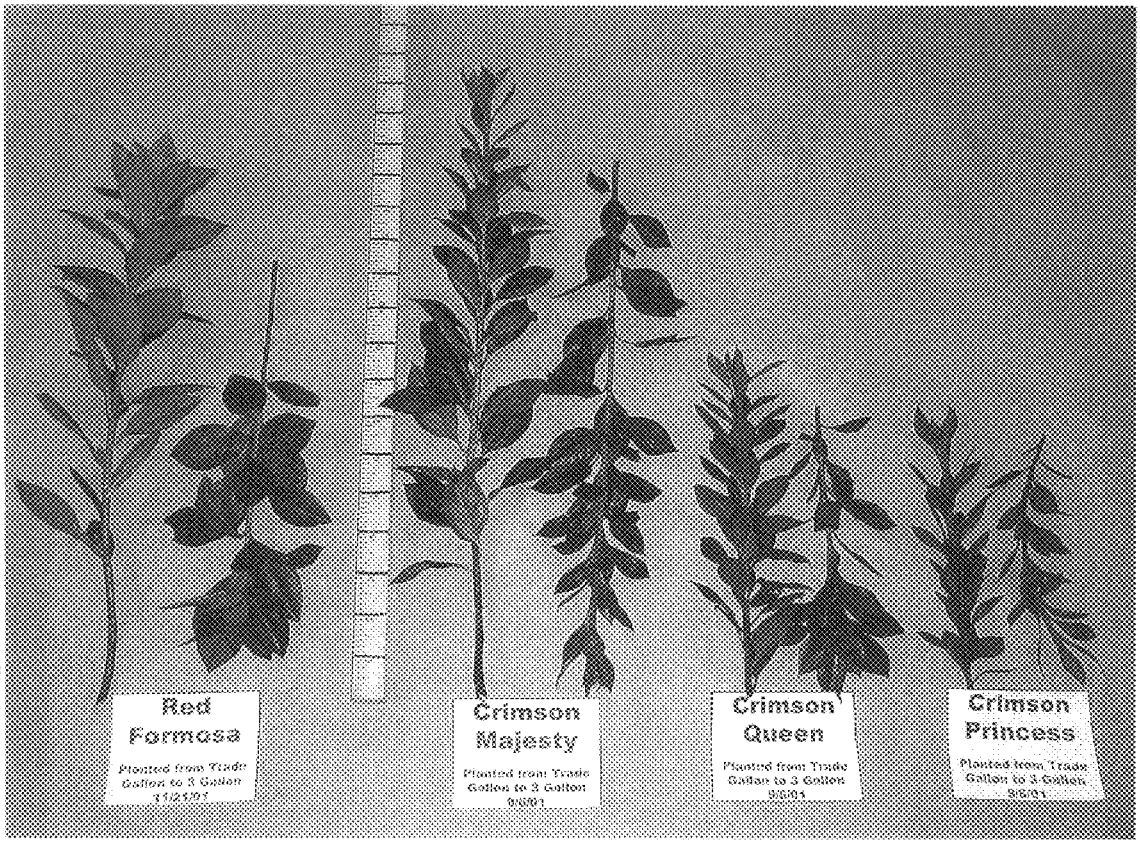

As a comparison, coloration of 'Red Formosa' is as follows: leaves upper surface, grayed-green group, N189A; leaves lower surface, green group, 138A; stem coloration 138-B Green group; bark coloration, 177-B Grayed-orange group; petiole coloration 138-B, 138-C Green Group. See FIG. 4 and 5.

Indumentum: The indumentum or plant hairs (trichomes) are hirsute in nature, i.e. the individual hairs are uniseriate, slender, tapering at the tip and arising more or less perpendicular to the epidermis, and becoming somewhat flexuous slightly above the leaf surface. The hairs give the leaves and twigs a somewhat bristly texture. The same type of hairs is present on both the upper and lower leaf surfaces. In terms of density the indumentum is characterized as being moderately pubescent with the hairs being spaced about 1/32 inch (0.5 mm) apart. On the lower surface the hairs are somewhat more closely spaced along the veins and petioles. Indumentum on the stems is similar except for the hairs being somewhat more closely spaced than on the leaf blade surfaces.

Fruit: None apparent.

Other:

*Petiole.*—Length 6–10 mm; diameter 1.5–3 mm wide, 1.5 mm thick; coloration: upper surface, 138-B Green Group with flecks of 59-ARed-Purple Group; lower surface 59-A Red Purple Group with flecks of 138 B Green Group.

*Fragrance.*—Insignificant — none apparent.

*Taste.*—Not relevant.

*Disease resistances.*—No known Azalea diseases observed to date on plants grown under commercial conditions. Expected to be similar to 'Red Formosa' cultivars — resistant to flower and leaf gall, caused by exobasidium vaccinii and root rot caused phytophthora cinnamomi; susceptible to Lace bug and to petal blight caused by ovulinia azalea.

*Seed production.*—Seed production has not been observed.

*Vigor.*—Similar to 'Red Formosa' cultivars, hardy in zones 7–9.

I claim:

1. A new and unique variety of Azalea plant named 'Crimson Queen' as herein shown and described.

* * * * *